United States Patent [19]

Harms et al.

[11] 4,194,504

[45] Mar. 25, 1980

[54] WINGED CATHETER PLACEMENT ASSEMBLY

[75] Inventors: Jack L. Harms, Mundelein; Charles H. Seberg, Libertyville, both of Ill.

[73] Assignee: Abbott Laboratories, North Chicago, Ill.

[21] Appl. No.: 950,941

[22] Filed: Oct. 12, 1978

[51] Int. Cl.² .............. A61M 5/00

[52] U.S. Cl. .............. 128/214.4; 128/DIG. 16

[58] Field of Search .............. 128/214 R, 214.4, 221, 128/348, 347, DIG. 16

[56] References Cited

U.S. PATENT DOCUMENTS

| | | | |
|---|---|---|---|
| 2,725,058 | 11/1955 | Rathkey | 128/221 |
| 3,064,648 | 11/1962 | Bujan | 128/214 R |
| 3,537,451 | 11/1970 | Beck et al. | 128/214.4 |
| 3,589,361 | 6/1971 | Loper et al. | 128/214.4 |
| 3,769,975 | 11/1973 | Nimoy et al. | 128/214.4 |
| 3,875,938 | 8/1975 | Mellor | 128/214.4 |
| 3,906,946 | 9/1975 | Nordstrom | 128/214.4 |

OTHER PUBLICATIONS

Deseret Company Brochure, Jan. 78, Angio-Set ®, Sandy, Utah.

*Primary Examiner*—Dalton L. Truluck

*Attorney, Agent, or Firm*—Robert L. Niblack; Aaron L. Hardt

[57] ABSTRACT

A needle-inside, catheter placement assembly including a needle and a catheter unit comprising a catheter, winged catheter insertion means, flexible tubing and tube hub, wherein an area of reduced thickness on each wing of the insertion means provides improved flexibility for the wing and the needle is captured within the winged catheter insertion means when the wings are simultaneously held in a vertical position.

8 Claims, 13 Drawing Figures

4 7 31 25 36 37 27 23 30 36 37 32 4 7 31 32 25 30 11

WINGED CATHETER PLACEMENT ASSEMBLY

BACKGROUND OF THE INVENTION

The present invention relates to intravenous catheter placement assemblies and, more particularly, to needle-inside, winged catheter placement assemblies.

U.S. Pat. No. 2,725,058 granted to A. Rathkey on Nov. 29, 1955 and U.S. Pat. No. 3,064,648 granted to A. Bujan on Nov. 20, 1962 disclose winged, intravenous needle assemblies. These needles serve as both a vein puncturing means and medical solutions conduit when used for intravenous solutions administration. Due to the necessary rigidity of these needles and their sharpened ends, it is common to immobilize that part of the patient into which the needle is inserted to avoid inadvertent damage to the patient's vein. If the needle remains inserted for extended periods of time, such continued immobilization results in stiffness and other discomfort to the patient.

U.S. Pat. No. 3,589,361 granted to D. Loper on June 29, 1971 discloses a needle-inside, winged catheter placement assembly which seeks to obviate the disadvantages of the Rathkey and Bujan needles. The Loper device comprises a needle concentrically located inside a flexible catheter which has a winged insertion means slidably affixed thereon and a hub affixed to its proximal end. When a patient is to be administered an intravenous solution, the winged insertion means is used to insert the needle and catheter into the patient's vein. The needle is then withdrawn from the catheter and the vein and the catheter adhered to the patient's body by means of the slidable wings.

An inherent disadvantage of the Loper device is that its catheter hub is located so near the venipunture wound that inadvertent manipulation of the catheter can occur during attachment of the intravenous solution administration tubing to the hub, resulting in irritation of, or damage to, the tissue at the wound site. U.S. Pat. No. 3,769,975 granted Nov. 6, 1973 to M. Nimoy, et al. discloses a needle-inside, winged catheter placement unit that obviates the above-stated inherent disadvantage of the Loper device by means of a flexible tubing extending from the proximal end of its winged insertion means and having a tubing hub at its proximal end.

An inherent disadvantage of the Nimoy device is that it requires the use of an extraneous sleeve positioned over the flexible tubing to prevent displacement of the wing section toward the tubing hub during the catheterization procedure. The need for such a sleeve requires additional costs and steps in the assembling and use of the Nimoy device. Accordingly, it will be apparent that such a needle-inside, winged catheter placement assembly without need of the extraneous sleeve would be advantageous and desirable.

SUMMARY OF THE INVENTION

Therefore, it is the primary object of this invention to provide a needle-inside, winged catheter placement assembly of the type disclosed by Nimoy, but without the need of an extraneous sleeve to prevent displacement of the winged catheter insertion means towards the tubing hub during the catheterization procedure.

In accordance with these and other objects, there is provided by the present invention, a winged intravenous catheter assembly including a needle and a catheter unit. The catheter unit comprises a flexible plastic catheter having a distally tapered distal end and a winged catheter insertion means including a tubular body having a lumen therethrough and a pair of wings having substantially uniform thickness extending oppositely therefrom. The proximal end of the catheter is in communication with the lumen of the catheter insertion means via its distal end. The catheter unit further comprises a flexible tubing having its distal end in communication with the lumen of the catheter insertion means via its proximal end and a tube hub having a lumen therethrough. The proximal end of the flexible tubing is in communication with the lumen of the tube hub via its distal end.

The needle is inserted through the catheter, winged catheter insertion means, flexible tubing and tube hub, and has a sharpened distal end extending beyond the distal end of the catheter and a proximal end attached to a needle hub.

Surprisingly, it has been found that the displacement of the winged catheter insertion means toward the tube hub present in prior art devices is obviated by locking the winged catheter insertion means to the needle during the venipuncture. The temporary locking is achieved by providing the lumen of the winged catheter insertion means a diameter opposite the portions of the wings adjacent the tubular body that is predetermined to capture the needle within the tubular body by the distortion of the lumen thereof when the wings are simultaneously held in a substantially vertical position. An area of reduced thickness on each of the wings substantially adjacent to the tubular body provides improved flexibility to the wings.

BRIEF DESCRIPTION OF THE DRAWING

Other objects and attendant advantages will be obvious to those skilled in the art by reading the following detailed description in connection with the accompanying drawing wherein like reference characters designate like or corresponding parts throughout the several figures thereof and wherein.

DETAILED DESCRIPTION OF THE INVENTION

Figure 1:
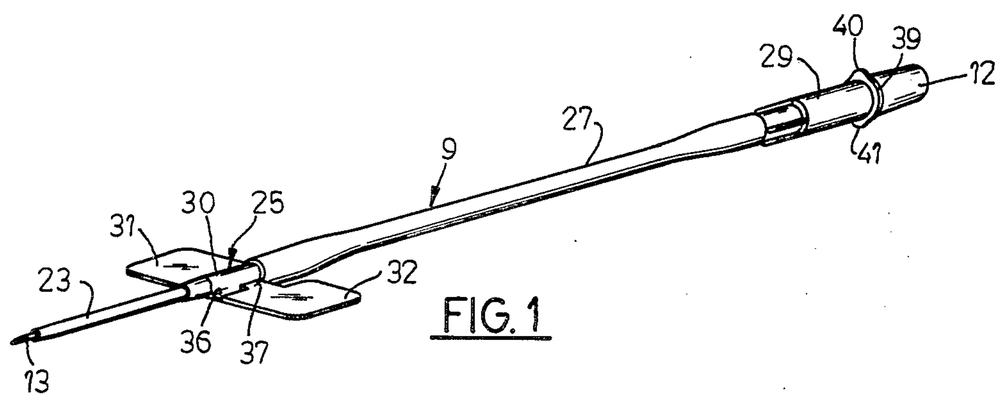
FIG. 1 is a perspective view of a preferred embodiment of the needle-inside, winged catheter placement assembly of the present invention.
Figure 2:
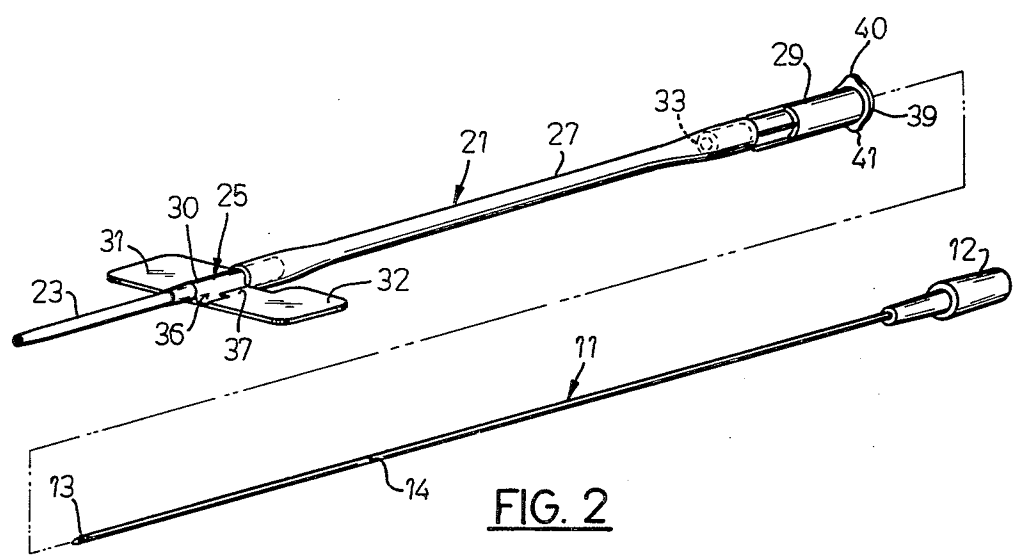
FIG. 2 is an exploded view of the assembly of FIG. 1 showing the catheter unit and the needle thereof.
Figure 3:
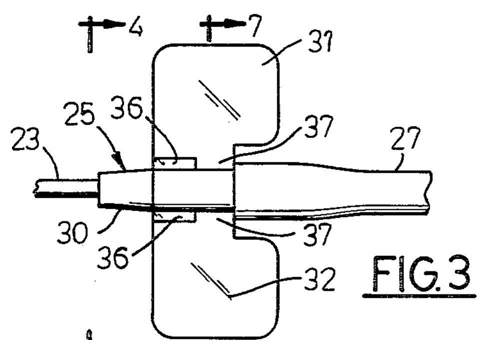
FIG. 3 is a top view of a portion of the assembly of FIG. 1 showing the reduced portions of the wings thereof.
Figure 4:
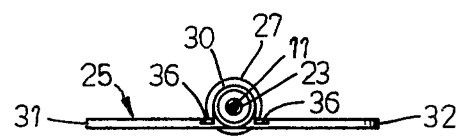
FIG. 4 is a cross-sectional view along the line 4—4 in FIG. 3 of the assembly thereof.

Referring to the drawing, there is shown in FIG. 1 a preferred embodiment of the needle-inside, winged catheter placement assembly 9 of this invention. Winged catheter placement assembly 9 comprises a needle 11 having its proximal end attached to a needle hub 12 and a beveled, sharpened distal end 13, as best seen in FIG. 2.

Preferably, needle 11 is made of a hollow, cylindrical stainless steel tube. However, it will be readily apparent to those skilled in the art, that the perimeter of needle 11 can have various configurations, or even a plurality of configurations along its length, if so desired. Preferably, needle 11 can have an aperture 14 opening into its lumen to allow the passage of blood from distal end 13 through aperture 14.

Catheter placement assembly 9 further comprises a catheter unit 21 having a plastic catheter 23, winged catheter insertion means 25, flexible tubing 27 and tube hub 29. Catheter 23 is distally tapered at its distal end and can be made of any biocompatible flexible plastic material such as polyethylene, polypropylene, polytetrafluorethylene, polyfluorinated ethylene propylene, or polyvinylchloride. The inner diameter of catheter 23 is substantially identical to the outer diameter of the portion of needle 11 that it encircles.

Winged catheter insertion means 25 has a tubular body 30 having a lumen therethrough and a pair of flexible wings 31, 32 oppositely extending therefrom. Wings 31, 32 have substantially uniform thickness, except for an area of reduced thickness 36 along a portion of the width on each wing substantially adjacent to tubular body 30. The reduced thickness 36 provides improved flexibility for wings 31, 32 which otherwise tend to bow rather than bend when moved in a vertical direction.

Figure 5:
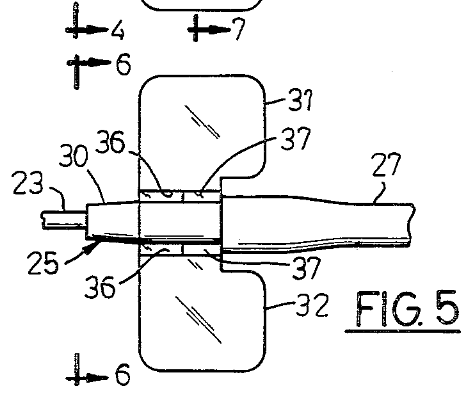
FIG. 5 is a top view of a portion of another embodiment of the winged catheter insertion means of the needle-inside, winged catheter placement assembly of the present invention showing the reduced portions of the wings thereof.
Figure 6:
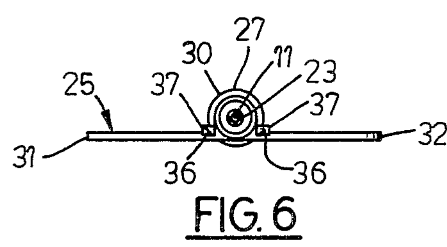
FIG. 6 is a cross-sectional view along the line 6—6 in FIG. 5 of the assembly thereof.

The remaining unreduced portions 37 of wings 31, 32 adjacent to tubular body 30, preferably, have the same thickness as the remainder of the wing. However, as illustrated in FIGS. 5 and 6, the unreduced portions 37 of wings 31, 32 may have a greater thickness than the remainder of the wing, if so desired.

The proximal end of catheter 23 is in communication with the lumen of tubular body 30 of the winged catheter insertion means 25 via its distal end. The lumen of tubular body 30 has a diameter opposite, at least, the unreduced portions of wings 31, 32 adjacent to tubular body portion 30 predetermined to only capture needle 11 within tubular body 30 by distortion of the lumen when wings 31, 32 are simultaneously held in a substantially vertical position.

Figure 7:
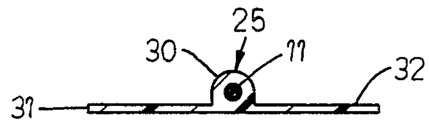
FIG. 7 is a cross-sectional view along the line 7—7 in FIG. 3 of the assembly thereof when the wings are in a horizontal position.
Figure 8:
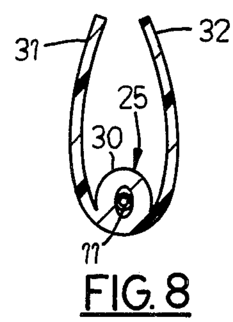
FIG. 8 shows the assembly of FIG. 7 when the wings thereof have been simultaneously raised to a substantially vertical position.
Figure 9:
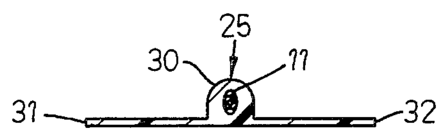
FIG. 9 is a cross-sectional view similar to FIG. 7 wherein the lumen of the winged catheter insertion means is noncylindrical when the wings are in a horizontal position.

As illustrated in FIGS. 7–9, needle 11 has an outer diameter substantially identical to the diameter of the lumen of tubular body 30 when wings 31, 32 are horizontal. When wings 31, 32 are simultaneously held in a substantially vertical position, the diameter of the lumen of tubular body 30 is decreased horizontally due to distortion and needle 11 is captured therein. While needle 11 and the lumen of tubular body 30 can be cylindrical, it will be apparent to those skilled in the art that either or both of them can be noncylindrical, so long as their diameters are predetermined to capture needle 11 when wings 31, 32 are simultaneously held in a substantially vertical position, as shown in FIG. 9.

Figure 10:
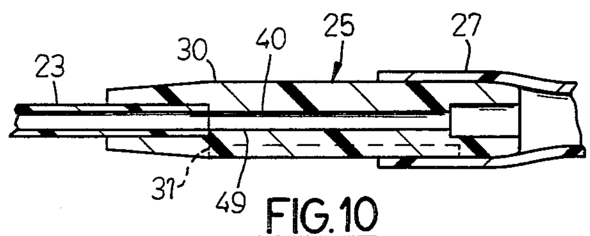
FIGS. 10–12 are cross-sectional views along a vertical plane through the axis of three embodiments of the catheter unit of the present invention illustrating the predetermined diameter of the lumen of the winged catheter insertion means thereof.
Figure 11:
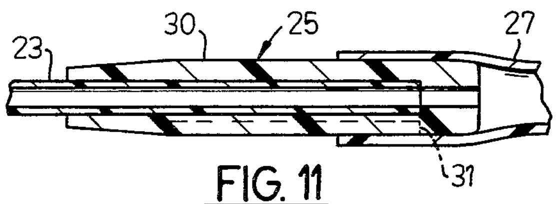

As illustrated in FIG. 10, the predetermined diameter of the lumen of tubular body 30 opposite unreduced portions 37 of wings 31, 32 can be formed as an integrally molded step 49 in the wall of tubular body 30. Alternatively, as shown in FIG. 11, catheter 23 can be extended into tubular body 30 to a location proximal to unreduced portions 37 so that needle 11 is actually captured within catheter 23 and the lumen of tubular body 30 when wings 31, 32 are simultaneously held in a substantially vertical position.

Figure 12:
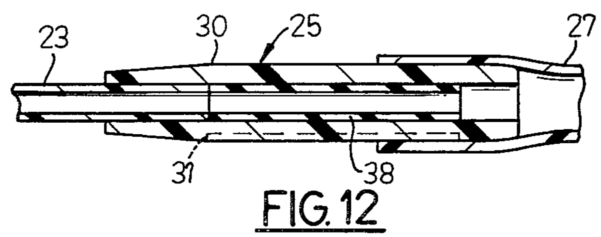
Figure 13:
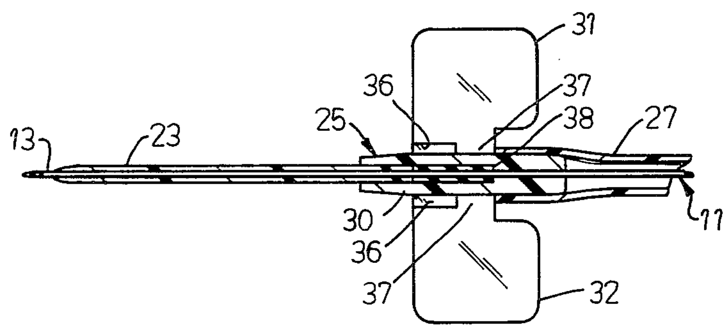
FIG. 13 is a cross-sectional view along a horizontal plane through the axis of a winged catheter placement assembly having an insertion means of the type illustrated in FIG. 12.

Preferably, as shown in FIGS. 12–13, the predetermined diameter of the lumen of tubular body 30 opposite unreduced portions 37 can be formed by a bushing 38 adhered thereto. Advantageously, bushing 38 allows a single winged catheter insertion means 25 to be employed with a plurality of needle diameters by merely choosing an appropriate bushing diameter for the desired needle.

As shown in FIG. 1, catheter 23 has an outer diameter substantially equal to the inner diameter of the lumen of tubular portion 30 and is inserted therein. However, it will be readily apparent that tubular portion 30 can be designed to receive catheter 23 on its outer diameter, if so desired.

The distal end of flexible tubing 27 is in fluid communication with the lumen of tubular portion 30 at its proximal end. As shown in FIG. 1, tubular portion 30 is inserted into flexible tubing 27, but it will be readily apparent that flexible tubing 27 can be inserted into tubular portion 30, if so desired. Preferably, flexible tubing 27 can be made of clear polyvinylchloride or polyurethane and has an inner diameter greater than the inner diameter of catheter 23.

The proximal end of flexible tubing 27 is connected in fluid communication to tube hub 29 which has a lumen 33 therethrough. Tube hub 29 is, preferably, made of polyvinylchloride, ABS copolymers or polycarbonate and, preferably, has a recess or female luer adapter at its proximal end. A collar 39 having ears 40, 41 extends outwardly from the proximal endwall of tube hub 29.

On assembly, needle 11 is inserted into catheter unit 21 until needle hub 12 can advance no further into or towards tube hub 29. At that time, the bevel at distal end 13 of needle 11, preferably, should be facing upwardly and projecting from the distal end of catheter 23 a chosen predetermined distance. If needle 11 has an aperture 14, it will then be situated within flexible tubing 27.

In use, it is anticipated that the catheter placement assembly 9 will be inserted into a patient by pinching flexible wings 31, 32 together and inserting the distal end of needle 11 and catheter 23 into the patient's vein in accordance with conventional venipuncture techniques well known in the medical practice. After the vein has been entered, if needle 11 is hollow and has an aperture 14, it will allow blood to flow, or flashback, to flexible tubing 27 where it will readily be visible to indicate that the vein has been entered.

After the venipuncture has been achieved, the person inserting the assembly into the patient presses wings 31, 32 flat against the patient with one hand and uses the other hand to grasp needle hub 12. Needle 11 is now free to be withdrawn from catheter unit 21 and discarded. Catheter 23 will have been fully inserted into the vein, wings 31, 32 taped to the patient, a safety loop formed with flexible tubing 27 and an intravenous solution set attached to tube hub 29 in accordance with conventional techniques of the medical practice.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

I claim:

1. In an intravenous catheter assembly including
(1) a catheter unit comprising:
(a) a flexible plastic catheter having a distally tapered distal end,
(b) a winged catheter insertion means comprising a resilient tubular body having a lumen therethrough and a pair of wings having substantially uniform thickness extending oppositely therefrom, the proximal end of said catheter in communication with said lumen of said catheter insertion means via its distal end,
(c) a flexible tubing having its distal end in communication with said lumen of said catheter insertion means via its proximal end,
(d) a tube hub having a lumen therethrough, the proximal end of said flexible tubing in communication with said lumen of said tube hub via its distal end, and
(2) a needle inserted through said catheter, winged catheter insertion means, flexible tubing and tube hub, said needle having a sharpened distal end extending beyond said distal end of said catheter and a proximal end attached to a needle hub; the improvement which comprises:
an area of reduced thickness on each of said wings along a portion of the width thereof substantially adjacent to said tubular body and providing improved flexibility to said wings, the remainder of said wing width portion providing an unreduced thickness portion, said lumen of said winged catheter insertion means having a diameter opposite the unreduced portions of said wings adjacent said tubular body predetermined to only capture said needle within said tubular body by the distortion of said lumen of said winged catheter insertions means when said wings are simultaneously held in a substantially vertical position.

2. The catheter assembly defined in claim 1 wherein the unreduced portions of said wings adjacent to said tubular body have a thickness greater than said substantially uniform thickness of said wings.

3. The catheter assembly defined in claims 1 or 2, wherein said diameter is substantially identical to the outer diameter of the portion of said needle inserted through said winged catheter insertion means.

4. The catheter assembly defined in claim 3, wherein said diameter is defined by an integrally molded wall of said tubular body.

5. The catheter assembly defined in claim 3, wherein said diameter is defined by a bushing attached to said tubular body.

6. The catheter assembly defined in claims 1 or 2, wherein said catheter extends into said lumen of said winged catheter insertion means to a location proximal to said unreduced portions of said wings adjacent to said tubular body, whereby said needle is captured within both said catheter and said tubular body when said wings are simultaneously held in a vertical position.

7. The catheter assembly defined in claims 1 or 2, wherein said lumen through said tubular body is noncylindrical when said wings are simultaneously disposed in a horizontal plane.

8. The catheter assembly defined in claims 1 or 2, wherein said needle further comprises an aperture intermediate of its proximal and distal ends through which blood can flow out of said needle.

* * * * *